US00PP13374P2

(12) United States Plant Patent
Johnson, Jr.

(10) Patent No.: US PP13,374 P2
(45) Date of Patent: Dec. 17, 2002

(54) PETUNIA PLANT NAMED 'COLORSPLASH'

(75) Inventor: Ozzie W. Johnson, Jr., Marietta, GA (US)

(73) Assignee: Itsaul Plants, Chamblee, GA (US)

( * ) Notice: Subject to any disclaimer, the term of this patent is extended or adjusted under 35 U.S.C. 154(b) by 0 days.

(21) Appl. No.: 10/103,951

(22) Filed: Mar. 22, 2002

(51) Int. Cl.[7] ..... A01H 5/00

(52) U.S. Cl. ..... Plt./356
(58) Field of Search ..... Plt./356

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Petunia plant named 'Colorsplash', characterized by its low-growing, mounded and outwardly spreading plant habit; green and pale yellow variegated leaves; and single flowers that are bright pink in color.

1 Drawing Sheet

BOTANICAL CLASSIFICATION/CULTIVAR DESIGNATION

*Petunia×hybrida* cultivar Colorsplash.

BACKGROUND OF THE INVENTION

The present Invention relates to a new and distinct cultivar of Petunia plant, botanically known as *Petunia×hybrida*, and hereinafter referred to by the cultivar name Colorsplash.

The new cultivar was discovered by the Inventor in a controlled environment in Chamblee, Ga. as a naturally-occurring branch mutation of the *Petunia×hybrida* cultivar Pink Wave, not patented. The new Petunia was observed on a plant within a population of plants of 'Pink Wave' in May, 1999. This branch mutation was selected on the basis of its unique leaf variegation.

Asexual reproduction of the new cultivar by terminal vegetative cuttings taken in Chamblee, Ga. since November, 2000, has shown that the unique features of this new Petunia are stable and reproduced true to type in successive generations.

SUMMARY OF THE INVENTION

Plants of the cultivar Colorsplash have not been observed under all possible environmental conditions. The phenotype may vary somewhat with variations in environment such as temperature and light intensity without, however, any variance in genotype.

The following traits have been repeatedly observed and are determined to be the unique characteristics of 'Colorsplash'. These characteristics in combination distinguish 'Colorsplash' as a new and distinct cultivar:

1. Low-growing, mounded and outwardly spreading plant habit.

2. Green and pale yellow variegated leaves.

3. Single flowers that are bright pink in color.

Plants of the new Petunia are most similar to plants of the parent cultivar. Plants of the new Petunia differ from plants of the cultivar Pink Wave primarily in foliage color as plants of the cultivar Pink Wave do not have variegated leaves. In addition, plants of the new Petunia grow slower than plants of the cultivar Pink Wave.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph differ slightly from the color values cited in the detailed botanical description which accurately describe the colors of the new Petunia. The photograph comprises a side perspective view of typical plant of 'Colorsplash' grown in a container.

DETAILED BOTANICAL DESCRIPTION

The cultivar Colorsplash has not been observed under all possible environmental conditions. The phenotype may vary somewhat with variations in environment such as temperature and light intensity without, however, any variance in genotype.

The aforementioned photograph, following observations and measurements describe plants grown during the spring in Chamblee, Ga., under commercial practice in a polyethylene-covered greenhouse. Plants were about 8 weeks from cuttings and were grown in 25-cm containers. During the production of the plants, day temperatures ranged from 23 to 33° C. and night temperatures ranged from 13 to 23° C.

In the following description, color references are made to The Royal Horticultural Society Colour Chart, 1995 Edition, except where general terms of ordinary dictionary significance are used.

Botanical classification: *Petunia×hybrida* cultivar Colorsplash.

Parentage: Naturally-occurring branch mutation of the *Petunia×hybrida* cultivar Pink Wave, not patented.

Propagation:

*Type cutting.*—Terminal vegetative cuttings.

*Time to initiate roots.*—Summer: About 4 days at 21° C. Winter: About 7 days at 15° C.

*Time to develop roots.*—Summer: About 28 days at 21° C. Winter: About 35 days at 15° C.

*Root description.*—Fine, fibrous, white in color.

*Rooting habit.*—Freely branching.

Plant description:

*Form.*—Annual flowering plant; indeterminate; low-growing, mounded and outwardly spreading; eventually cascading. Slow growth rate.

*Usage.*—Appropriate for hanging baskets, window boxes, patio containers and landscape applications.

*Plant height.*—About 10.5 cm.

*Plant diameter.*—About 37 cm.

*Branching habit.*—Freely branching with potentially one lateral branch forming at every node.

*Lateral branches.*—Length: About 18.5 cm. Diameter: About 3 mm. Internode length: About 1.5 cm. Texture: Pubescent; viscid. Color: 144A.

*Foliage description.*—Arrangement: Before flowering, alternate; after flowering, opposite; simple. Length: About 3.75 cm. Width: About 2.7 cm. Shape: Broadly ovate. Apex: Acute. Base: Obtuse with cuneate tendencies. Margin: Entire. Texture, upper and lower surfaces: Pubescent; leathery; glandular and viscid. Surface, upper and lower surfaces: Rugose. Fragrance: Herb-like. Venation pattern: Pinnate. Color: Young foliage, upper surface: Ground color, close to 5C to 5D; random light green, close to 146D, and darker green, close to 146A, flecks and spots. Young foliage, lower surface: Ground color, close to 5D to 4D; random light green, close to 147C, and darker green, close to 146C, flecks and spots. Fully expanded foliage, upper surface: Ground color, close to 4C to 4D; random light green, close to 147C, and darker green, between 146A and 147A, flecks and spots. Fully expanded foliage, lower surface: Ground color, close to 4D; random light green, close to between 146C and 147C, and darker green, close to 146A, flecks and spots. Venation, upper and lower surfaces: Same as lamina. Petiole length: About 5 mm. Petiole diameter: About 2.5 mm. Petiole color: 146B to 146C.

Flower description:

*Flower type and habit.*—Single salverform flowers; flowers face mostly upward or outward; axillary; potentially one flower per every node.

*Natural flowering season.*—Long day responsive; spring until frost in the autumn; flowering continuous. Flowers persistent.

*Flower longevity on the plant.*—About 4 days; flowers persistent.

*Fragrance.*—Herb-like.

*Flower size.*—Diameter: About 5.7 cm. Tube length: About 2.6 cm. Throat diameter, distal end: About 8 mm. Tube diameter, proximal end: About 3 mm.

*Flower buds (before showing color).*—Length: About 1.3 cm. Diameter: About 3 mm. Shape: Oblong. Color: 144A.

*Corolla.*—Quantity/arrangement: Five fused petals; funnelform. Petal length from throat. About 2.8 cm. Petal width: About 2.7 cm. Petal shape: Roughly spatulate. Petal apex: Acute with cuspidate tendencies. Petal margin: Entire. Petal texture, upper and lower surfaces: Smooth, satiny. Petal color: When opening, upper surface: 57A. When opening, lower surface: 57C to 57D. Fully opened, upper surface: Close to 68A; flower color fading to lighter than 68A with subsequent development. Fully opened, lower surface: 57D. Flower throat (inside): Close to 155D. Flower tube (outside): Close to 69D. Venation, upper petal surface: 57A. Venation, lower petal surface: Laterals, 57C to 57D; midvein, 144A. Venation, throat: Close to 144A. Venation, tube: 144A.

*Sepals.*—Arrangement/appearance: Single whorl of five sepals fused at base, star-shaped. Length: About 1.2 cm. Width: About 3 mm. Shape: Elongate, ligulate. Apex: Rounded. Margin: Entire. Texture, upper and lower surfaces: Pubescent. Color, upper and lower surfaces: 146A.

*Peduncles.*—Length: About 2 cm. Width: About 1 mm. Angle: Erect to 45° from vertical. Strength: Moderately strong; flexible and wiry. Texture: Pubescent. Color: 144A.

*Reproductive organs.*—Stamens: Quantity per flower: About five. Anther shape: Oblong, two-parted. Anther length: About 1 mm. Anther color: 4C. Pollen amount: Scarce. Pollen color: 4C. Pistils: Quantity per flower: One. Pistil length: About 2 cm. Style color: Close to 150D. Stigma shape: Rounded. Stigma color: Close to 144A. Ovary color: 144A.

*Seed/fruit.*—Seed nor fruit production has not been observed.

Disease/pest resistance: Plants of the new Petunia have not been noted to be resistant to pathogens or pests common to Petunia.

Temperature tolerance: Plants of the new Petunia have been observed to tolerate temperatures from 0 to 35° C.

It is claimed:

1. A new and distinct cultivar of Petunia plant named 'Colorsplash', as illustrated and described.

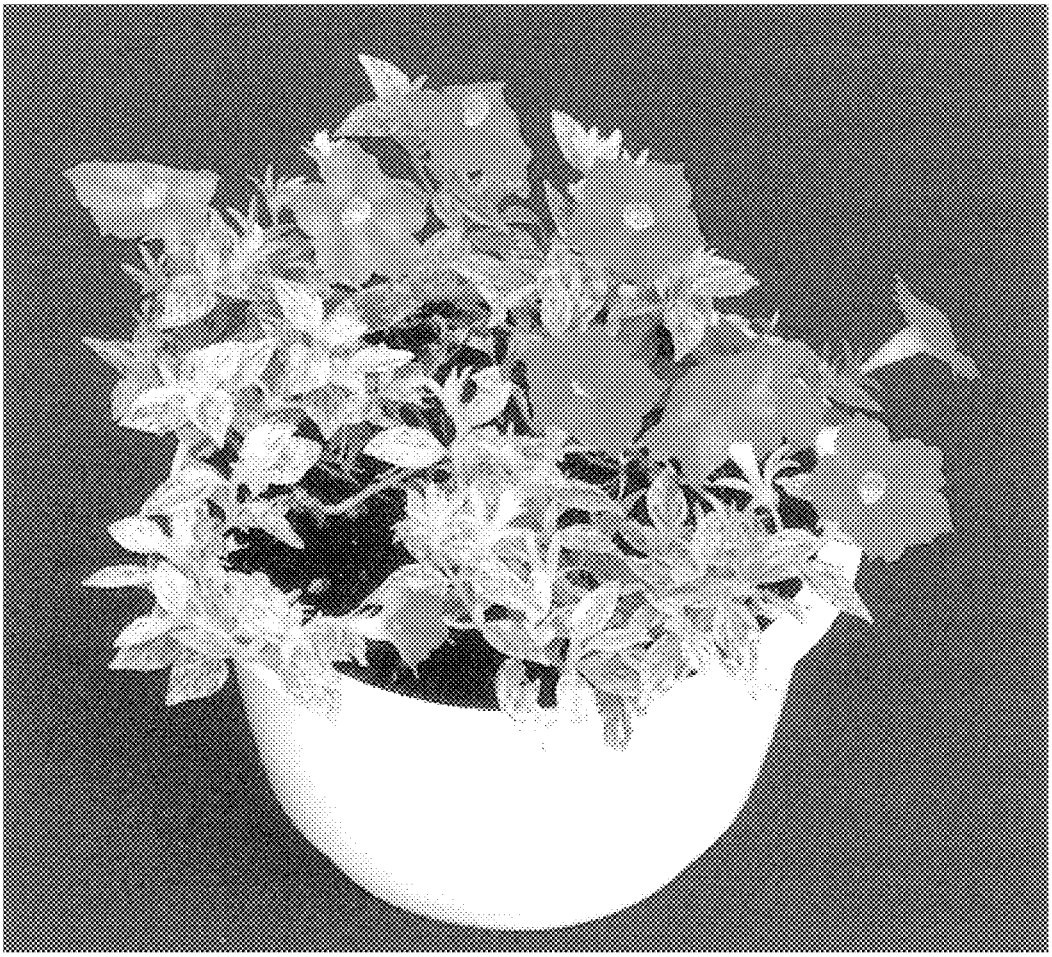

* * * * *